US008158112B2

(12) United States Patent
Fujinuma et al.

(10) Patent No.: US 8,158,112 B2
(45) Date of Patent: *Apr. 17, 2012

(54) HAIR COSMETIC PRODUCT

(75) Inventors: Hiroyuki Fujinuma, Tokyo (JP); Takashi Matsuo, Tokyo (JP); Masahiko Ogawa, Tokyo (JP); Tomohito Koshika, Tokyo (JP); Kazuhiro Okada, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/849,576

(22) Filed: Aug. 3, 2010

(65) Prior Publication Data

US 2010/0316583 A1  Dec. 16, 2010

Related U.S. Application Data

(62) Division of application No. 10/829,954, filed on Apr. 23, 2004.

(30) Foreign Application Priority Data

Apr. 25, 2003 (JP) .................................. 2003-122808

(51) Int. Cl.
  A61Q 5/08 (2006.01)
  A61Q 5/10 (2006.01)
(52) U.S. Cl. ........................ 424/62; 424/70.1; 424/70.19
(58) Field of Classification Search .................. None
  See application file for complete search history.

(56) References Cited

U.S. PATENT DOCUMENTS

| | | | |
|---|---|---|---|
| 3,341,418 A | 9/1967 | Moses et al. | |
| 3,709,437 A | 1/1973 | Wright | |
| 4,823,985 A | 4/1989 | Grollier et al. | |
| 4,961,925 A | 10/1990 | Tsujino et al. | |
| 5,143,518 A | 9/1992 | Madrange et al. | |
| 5,848,730 A | 12/1998 | Kawase et al. | |
| 5,968,486 A | 10/1999 | Newell et al. | |
| 7,938,864 B2* | 5/2011 | Miyabe et al. | 8/405 |
| 7,955,400 B2* | 6/2011 | Fujinuma et al. | 8/405 |
| 7,972,389 B2* | 7/2011 | Matsunaga et al. | 8/405 |
| 8,002,848 B2* | 8/2011 | Miyabe | 8/405 |
| 8,021,439 B2* | 9/2011 | Miyabe et al. | 8/405 |
| 8,025,702 B2* | 9/2011 | Fujinuma et al. | 8/405 |
| 8,025,703 B2* | 9/2011 | Ogawa et al. | 8/405 |
| 2004/0213752 A1 | 10/2004 | Fujinuma et al. | |
| 2010/0126522 A1 | 5/2010 | Fujinuma et al. | |
| 2010/0126523 A1 | 5/2010 | Fujinuma et al. | |
| 2010/0236570 A1 | 9/2010 | Fujinuma et al. | |
| 2010/0242187 A1 | 9/2010 | Miyabe | |
| 2010/0251488 A1 | 10/2010 | Fujinuma et al. | |
| 2010/0257677 A1 | 10/2010 | Miyabe et al. | |
| 2010/0299848 A1 | 12/2010 | Fujinuma et al. | |
| 2010/0313905 A1 | 12/2010 | Fujinuma et al. | |
| 2010/0316583 A1 | 12/2010 | Fujinuma et al. | |
| 2011/0073128 A1 | 3/2011 | Ogawa et al. | |

FOREIGN PATENT DOCUMENTS

| | | |
|---|---|---|
| DE | 1801518 | 1/1971 |
| EP | 113418 | 7/1984 |
| EP | 0 503 507 | 9/1992 |
| EP | 1 055 425 | 11/2000 |
| EP | 0 877 653 | 10/2002 |
| EP | 1291006 | 12/2003 |
| GB | 1125528 | 8/1968 |
| GB | 2 254 341 | 10/1992 |
| GB | 2 293 157 | 3/1996 |
| JP | 48-68750 | 9/1973 |
| JP | S49-050144 | 5/1974 |
| JP | 55-49308 | 4/1980 |
| JP | 58-30282 | 6/1983 |
| JP | 59-108710 | 6/1984 |
| JP | 61-143412 | 7/1986 |
| JP | 62-242609 | 10/1987 |
| JP | 63-246313 | 10/1988 |
| JP | 04-99711 | 3/1992 |
| JP | 04-282307 | 10/1992 |
| JP | 04-293568 | 10/1992 |
| JP | O6-107530 | 4/1994 |
| JP | 06-271435 | 9/1994 |
| JP | 6-271435 | 9/1994 |
| JP | 07-23293 | 3/1995 |
| JP | 07-267834 | 10/1995 |
| JP | 07-330559 | 12/1995 |
| JP | 07-330560 | 12/1995 |
| JP | 08-40837 | 2/1996 |
| JP | 08-119839 | 5/1996 |
| JP | 08-165235 | 6/1996 |
| JP | 8-199188 | 8/1996 |
| JP | 08-199188 | 8/1996 |
| JP | 08-230959 | 9/1996 |
| JP | 08-231345 | 9/1996 |
| JP | 8-231346 | 9/1996 |
| JP | 8-259426 | 10/1996 |

(Continued)

OTHER PUBLICATIONS

Notification of Reasons for Refusal dated Jul. 22, 2008.

(Continued)

Primary Examiner — Jyothsna Venkat
(74) Attorney, Agent, or Firm — Oblon, Spivak, McClelland, Maier & Neustadt, L.L.P.

(57) ABSTRACT

A hair cosmetic product has a two agent type hair cosmetic which comprises a first agent containing an alkali agent and a second agent containing hydrogen peroxide, wherein at least one of the first and second agents contains a surfactant; and a foamer vessel which discharges a mixed liquid comprising the first and second agents in the form of foam. Another hair cosmetic product has a two agent type hair cosmetic which contains a first agent that includes an alkali agent and a second agent that includes hydrogen peroxide, and which is used after mixing the first and second agents immediately prior to use, and a foamer vessel from which a mixed liquid of the first and second agents is discharged in the form of foam. A surfactant is contained in the mixed liquid at an amount of 0.1 to 10 wt %, and the viscosity of the mixed liquid at 25° C. is 1 to 300 mPa·s.

14 Claims, No Drawings

FOREIGN PATENT DOCUMENTS

| | | |
|---|---|---|
| JP | 08-268848 | 10/1996 |
| JP | 08-282308 | 10/1996 |
| JP | 8-283695 | 10/1996 |
| JP | 09-2923 | 1/1997 |
| JP | 09-2925 | 1/1997 |
| JP | 9-25223 | 1/1997 |
| JP | 09-40534 | 2/1997 |
| JP | 2579516 | 2/1997 |
| JP | 09-136818 | 5/1997 |
| JP | 09-143040 | 6/1997 |
| JP | 09-506130 | 6/1997 |
| JP | 09-227347 | 9/1997 |
| JP | 9-227347 | 9/1997 |
| JP | 09-234112 | 9/1997 |
| JP | 09-255541 | 9/1997 |
| JP | 9-255541 | 9/1997 |
| JP | 9-301835 | 11/1997 |
| JP | 10-25230 | 1/1998 |
| JP | 10-167938 | 6/1998 |
| JP | 10-287534 | 10/1998 |
| JP | 11-18836 | 1/1999 |
| JP | 11-18837 | 1/1999 |
| JP | 11-50089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-286421 | 10/1999 |
| JP | 2000-191471 | 7/2000 |
| JP | 2000-297018 | 10/2000 |
| JP | 2000-297019 | 10/2000 |
| JP | 2001-10930 | 1/2001 |
| JP | 2001-19626 | 1/2001 |
| JP | 2001-97834 | 4/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-20247 | 1/2002 |
| JP | 2002-97121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 2003-12479 | 1/2003 |
| JP | 2003-26554 | 1/2003 |
| JP | 2003-40747 | 2/2003 |
| JP | 2003-63936 | 3/2003 |
| JP | 2003-73240 | 3/2003 |
| JP | 2003-73241 | 3/2003 |
| JP | 2003-81369 A | 3/2003 |
| JP | 2003-081791 A | 3/2003 |
| JP | 2003-95900 | 4/2003 |
| JP | A1-2007-291015 | 11/2007 |
| JP | A1-2007-314523 | 12/2007 |
| JP | 2010-6803 | 1/2010 |
| JP | 2010-6805 | 1/2010 |
| WO | WO 91/14759 | 10/1991 |
| WO | WO 9516023 | 6/1995 |
| WO | WO 01/85105 | 11/2001 |
| WO | WO 01/85113 | 11/2001 |

OTHER PUBLICATIONS

Submission of Publication and the like dated Dec. 25, 2007.
Submission of Publication and the like dated Feb. 29, 2008.
"Food and Packaging", Can Technology Study Group, vol. 34, No. 8, Aug. 1, 1993, 6 pages.
English Translation of "Food and Packaging", Submission of Publications and the like dated Nov. 10, 2008.
Corresponding application filed in Japanese application No. 2004-130373 filed on Nov. 10, 2008.
Japanese Patent Office Communication, Apr. 21, 2009, 3pp. (Includes statement submitted by third party.).
Japanese Submission of Publications, Mar. 24, 2009.
Submission of Publication and the like dated Sep. 7, 2009.
JP 2002-284655 (Oct. 3, 2002) Abstract.
JP 8-283695 (Oct. 29, 1996) Abstract.
JP 10-287534 (Oct. 27, 1998) Abstract.
JP 9-227347 (Sep. 2, 2007) Abstract.
Third Party Observation issued on May 3, 2011 in corresponding European Application No. 04 009 836.
Extended Search Report issued Nov. 4, 2010 in European Application No. 10172766.7.
Submission of Publication issued Oct. 18, 2010 in JP Application No. 2004-130373 (With English Translation).
Office Action issued Nov. 5, 2010 in EP Application No. 04 009 836.0.
Extended European Search Report issued Apr. 7, 2011, in European Patent Application 10183376.2-2108.
Extended European Search Report issued in Nov. 4, 2010 in European Patent application No. 10172766.7.
Submission of Publications filed Oct. 18, 2010 in Japanese application No. 2004-130373 (w/English Translation).
Communication Pursuant to Article 94(3) EPC issued Nov. 5, 2010 in European Patent application No. 0 400 9836.0.
Submission of Publications filed Oct. 25, 2010 in Japanese application No. 2008-270377 (w/English Translation).
Decision of Refusal issued Jun. 16, 2010 in Japanese application No. 2004-130373 (w/English Translation).
Written Demand for Appeal filed Sep. 10, 2010 in Japanese application No. 2004-130373 (w/English Translation).
Amendment filed Sep. 10, 2010 in Japanese application No. 2004-130373 (w/English Translation).
Submission of Publications filed Apr. 8, 2009 in Japanese application No. 2004-130373 (w/English Translation).
English Translation of Decision to Grant a Patent issued Jan. 4, 2011 in Japanese Patent application No. 2004-130373 w/Allowed Claims.
English Translation of Decision to Grant a Patent issued Jan. 4, 2011 in Japanese Patent application No. 2008-270377 w/Allowed Claims.
English translation of Remarks filed Oct. 20, 2008 in Japanese application No. 2004-130373.
English translation of Remarks filed Mar. 9, 2009 in Japanese application No. 2004-130373.
English translation of Amendment filed Mar. 9, 2009 in Japanese application No. 2004-130373.
English translation of Submission of Publications filed Sep. 7, 2009 in Japanese application No. 2004-130373.
English translation of Submission of Publications filed Mar. 24, 2009 in Japanese application No. 2004-130373.
English translation of Submission of Publications filed Nov. 10, 2008 in Japanese application No. 2004-130373.
English translation of Notification of Reasons for Refusal issued Jan. 6, 2009 in Japanese application No. 2004-130373.
English translation of Notification of Reasons for Refusal issued Jul. 22, 2008 in Japanese application No. 2004-130373.
English translation of Submission of Publications filed Dec. 25, 2007 in Japanese application No. 2004-130373.
English translation of Submission of Publications filed Feb. 29, 2008 in Japanese application No. 2004-130373.
Response to Communication Pursuant to Article 96(2) EPC filed Apr. 25, 2007 in European Patent application No. 0 400 9836.0.
Communication Pursuant to Article 94(3) EPC issued Dec. 29, 2008 in European Patent application No. 0 400 9836.0.
Response to Communication filed Jul. 8, 2009 in European Patent application No. 0 400 9836.0.
Third-Party Observation filed on Dec. 19, 2009 in European Patent application No. 0 400 9836.0.
Observations under Rule 114(2) EPC filed Apr. 9, 2010 in European Patent application No. 0 400 9836.0.
Third-Party Observation filed on May 10, 2010 in European Patent application No. 0 400 9836.0.
Communication Pursuant to Article 94(3) EPC issued Jun. 28, 2010 in European Patent application No. 0 400 9836.0.
Response to Communication filed Aug. 10, 2010 in European Patent application No. 0 400 9836.0.
Amendment filed Dec. 5, 2008 in European Patent application No. 0 400 9836.0.
Response to Communication filed Feb. 18, 2011 in European Patent application No. 0 400 9836.0.

Remarks filed Feb. 25, 2011 in European Patent application No. 0 400 9836.0.
Experimental Report 1 (with English translation), served on May 24, 2011, in regard to Heisei 23 year (Yo) No. 22009.
Nakanishi, Fumio. Fragrance Journal. "Function of Recent Hair Coloring Agent and Developmental Trend Thereof." Aug. 15, 2001. pages 39-45. (with English translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).
Tashima, Masaru, et al. Fragrance Journal. "Research and Development of Mist Foam Type Hair Styling Product." Dec. 15, 1992. pp. 61-69. (with English translation).
Omura, Takayuki, et al. Fragrance Journal. "Development Trend and Problems of Recent Hair Foam." Mar. 15, 1994. pp. 29-35. (with English translation).
Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 36, No. 3. Non-Gas Container Having Increased Level of Accomplishment (Part 3). 1995. pp. 154-158. (with English translation).
Prettia Product Information (with English Translation), Kao Corporation, published after Apr. 23, 2003. (served on May 25, 2011 in regard to Heisei 23 year (Yo) No. 22009).
Instructions for Feminine Treatment Hair Color (with English Translation), Feminine Co Ltd., published before Apr. 23, 2003 (served on May 25, 2011 in regard to Heisei 23 year (Yo) No. 22009).
Feminine Treatment Hair Color 84, Certification for Approval for Manufacture of Quasi-Drug (with English Translation), Jan. 30, 1997.
Instructions for Feminine Retouch Color (with English Translation), Feminine Co., Ltd., published before Apr. 23, 2003. (served on May 25, 2011, in regard to Heisei 23 year (Yo) No. 22009).
Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Test Report 4 (with English translation), served on Jul. 10, 2011, in regard to Helsel 23 year (Yo) No. 22009.
Mottram, F.J., et al. Poucher's Perfumes, Cosmetics and Soaps, 10th ed. © 2000. "Hair Shampoos." pp. 295-301.
Handbook "Poly Haarberater Coloration," original edition, 1992. pp. 76-77.
Third-Party Observation submitted May 12, 2011, in European Patent Application No. 04009836.0.
371-EPO Response in European Patent Application No. 04009836.0, Jun. 15, 2011.
Reply to EESR in European Patent Application No. 10172766.7, Apr. 29, 2011.
Third-Party Observation submitted Jun. 24, 2011, in European Patent Application No. 10172766.7.
Third-Party Observation submitted Jun. 24, 2011, in European Patent Application No. 10183376.2.
Shinbiyo Marcel, Oct. 1996, No. 31, pp. 73 and 83, "Vivid Highlight" advertisement p. (with partial English translation).
Vivid Highlight, Iriya Cosmetics, Packaging and Instructions Insert, Sep. 6, 1996 (with English translation).
Hair Mode, Aug. 1996, No. 437, p. 108 (with partial English translation).
Decision to Refuse a European Patent Application issued Apr. 19, 2011 in regard to European Patent Application No. 08752171.2, filed Apr. 25, 2008.
Third-Party Observation submitted Jun. 3, 2011, in European Patent Application No. 10172766.7, filed Apr. 26, 2004.
Rompps Chemie Lexikon, vol. 6, 8th Ed. 1998, p. 4531.
Photocopy of a folding, collapsible box for "Poly Brillance Intensiv-Color-Creme", dated as Aug. 25, 1997.
Instructions for use contained in the folding, collapsible box for "Poly Brillance Intensiv-Color-Creme" Aug. 25, 1997.
Entire contents of the folding, collapsible box for "Poly Brillance Intensiv-Color-Crème" Aug. 25, 1997.
Close-up photocopy of the folding, collapsible box for "Poly Brillance Intensiv-Color-Crème" Aug. 25, 1997.
Henkel Study Report, Study No. 1100546-2. "Single Application Epicutaneous Patch Test (24th Patch Test)," served on Jan. 30, 2012, in regard to No. 22009, 2011 (yo).
Henkel Study Report, Study No. 1100546-1. "Open Epicutaneous Test," served on Jan. 30, 2012, in regard to No. 22009, 2011 (yo).
Henkel Study Report. "In Vitro Skin Irritation Test: Human Skin Model Test," served on Jan. 30, 2012, in regard to No. 22009, 2011 (yo).
Study Report, No. 1100547-1, "Dermatological Use Test with Hair-Coloring Products in Split Design," served on Jan. 30, 2012, in regard to No. 22009, 2011 (yo).
Experimental Result Report 13 (with English translation), served on Jan. 30, 2012, in regard to No. 22009, 2011 (yo).
Submission of Publications and the like, dated Nov. 10, 2008, in Japanese Patent Application No. 2004-130373.
European Patent Office Communication pursuant to Rule 114(2) EPC issued May 3, 2011, in European Application No. 04009836.0 filed Apr. 26, 2004.
Third-Party Observation filed on Apr. 27, 2011, in European Patent Application No. 0 400 9836.0 (including translation of submission).
European Search Report submitted Aug. 23, 2004, in European Patent Application No. 04009836.0.
Sato, Takatoshi. Science of Cosmetics. Mar. 20, 1997. pp. 138-140. (with English translation).
Quasi Drugs Manufacturing Material Specification 2006, first edition. pp. 527-528. Jun. 16, 2006. (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
Denavarre, Maison G. The Chemistry and Manufacture of Cosmetics, second edition, vol. 4. 1975. pp. 841-863.
Cosmetics Dictionary, first edition. Oct. 1, 1992. page 373. (with English translation).
Miyagi, Takashi. Food and Packaging, vol. 42, No. 10. "Growing Pump Foamer Spreading into Western Markets, Part One: Mini-Foamer." Oct. 1, 2001. pp. 609-613. (with English translation).
English translation of Submission of Publications and the like, filed Feb. 29, 2008, in Japanese Application No. 2004-130373.
English translation of Submission of Publications and the like, filed Dec. 25, 2007, in Japanese Application No. 2004-130373.
Comprehensible Surfactant, first edition. Sep. 1, 2003. pp. 32-49. (with English translation).
Taya-A.T. HM Education Mook., Series 3. "Knowing Mechanisms of Hair Coloring Agents." Apr. 10, 1998. pp. 8-9. (with English translation).
Nakanishi, Fumio. Fragrance Journal. "Future View of Hair Care Products." Jan. 15, 1997. pp. 49-56. (with English translation).
Sato, Takatoshi, et al. Fragrance and Cosmetics Science. "Permanent Hair Colorant." Sep. 20, 2001. pp. 138-140. (with English translation).
Watanabe, Yasushi, et al. Hair Science. "Hair Colorant." Feb. 1, 1986. pp. 144-150. (with English translation).
Kishi, Haruo. Modern Fragrance and Cosmetics Science, 1st Edition. Mar. 20, 1979. pp. 42-47. (with English translation).
Cosmetics Handbook. Nov. 1, 1996. pp. 220-221, 441-444. (with English translation).
Handbook—Raw Materials of Cosmetics and Drugs—revised edition. Feb. 1, 1977. pp. 358-361. (with English translation).
Yasuda, Kosaku, et al. Knowledge of Fat and Oil Products. Aug. 25, 1977. pp. 240-244. (with English translation).
Mitsui, Takeo. New Cosmetic Science. Jan. 12, 1993. pp. 137-142. (with English translation).
The Handbook of Oil Chemistry, 4th ed. "Lipids and Surfactants." Nov. 20, 2001. p. 522. (with English translation).
Comprehensive Dictionary of Chemistry. Oct. 20, 1989. pp. 56, 60-61, 646-647, 1762-1763. (with English translation).
Sato, Takatoshi, et al. Fragrance and Cosmetics Science. Mar. 20, 1997. pp. 73-74. (with English translation).

Japanese Collection of General Raw Materials for Cosmetics, fourth edition. Oct. 31, 1997. p. 583. (with English translation).

Analytical Chemistry Handbook, revised second edition. Oct. 10, 1971. p. 27-29. (with English translation).

Analysis Methods for Surfactants. Oct. 1, 1975. pp. 117-118. (with English translation).

New Cosmetic Science, second edition. Jan. 18, 2001. pp. 152-153. (with English translation).

"Make Your Hair Beautiful by Correct Usage—Hair Coloring ABC, revised edition." Feb. 1, 2000. pp. 18-19. (with English translation).

Robbins, Clarence R. "Chemical and Physical Behavior of Human Hair, fourth edition." Jul. 10, 2006. pp. 221-231. (with English translation).

Experimental Result Report 8 (with English translation), served on Nov. 29, 2011, in regard to No. 22009, (yo).

Fragrance Journal. vol. 19, No. 6. "Recent Progress of Hair Dyes and Problems in Research and Development." Jun. 15, 1991. pp. 26-27. (with English translation).

Miyagi, Takashi. Food and Packaging, vol. 34, No. 9. "Will Non-Gas Containers Create a Boom? (No. 3)" 1993. pp. 531-535. (with English translation).

Chemical Daily. "Surfactant—Penetrated to the various fields taking advantage of unique characteristics." Jan. 21, 1999. (with English translation).

The Nikkan Kogyo Shimbun, Ltd. "Nonylphenol Identified as Endocrine Disrupting Chemical." Aug. 6, 2001. (with English translation).

Chemical Daily. "Surfactant—Started growing responding to safety requirement." Jan. 19, 2000. (with English translation).

Chemical Daily. "Surfactant—Remarkable performance of non-ionic surfactant (Market conditions in chemicals)." Jan. 25, 2002. (with English translation).

Nakanishi, Fumio, et al. Science History of Hair Dye. Jan. 8, 1991. pp. 45-47. (with English translation).

Experiment Result Report 1 (with English translation), prepared on Jul. 11, 2011, in regard to No. 22009, (yo).

Experimental Result Report 2 (with English translation), prepared on Jul. 22, 2011, in regard to No. 22009, (yo).

Declaration by Akiko Nagabuchi (with English translation), served on Sep. 21, 2011, in regard to No. 22009, (yo).

Experiment Result Report 5 (with English translation), served on Sep. 21, 2011, in regard to No. 22009, (yo).

Arai, Yasuhiro. "State-of-the-art: Hair Color Technology—Trends in development as seen in patents." Published by Fragrance Journal Ltd. Aug. 25, 2004. pp. 102-105, 212-213. (with English translation).

Experimental Result Report 6 (with English translation), served on Sep. 21, 2011, in regard to No. 22009, (yo).

Experimental Result Report 7 (with English translation), served on Sep. 21, 2011, in regard to No. 22009, (yo).

Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).

Written Argument filed by the Debtor (1/2) in The Case of Request for Provisional Disposition of Patent Right: No. 22056, (yo), served on Sep. 6, 2011. pp. 1-5, 29-34. (with partial English translation).

Amendments to the Claims in Japanese Patent Application No. 2010-268209, filed on Apr. 8, 2011. (with English translation).

Publication of Unexamined Patent Application JP 2003-81369, Mar. 19, 2003.

English translation of Submission of Publications and the like, filed Mar. 24, 2009, in Japanese Application No. 2004-130373.

English translation of Submission of Publications and the like, filed Nov. 10, 2008, in Japanese Application No. 2004-130373.

English translation of Notification of Reasons for Refusal issued Jul. 22, 2008, in Japanese Application No. 2004-130373.

Iwakura, Ryouhei. "Present State and Problems of Hair Dyes." Fragrance Journal, Special Issue. No. 11, pp. 87-93. Dec. 25, 1990. (with English translation).

Ishikawa, Ryoji. Experimental Report, in regard to No. 22056, (yo). Dec. 28, 2011. (with English translation).

Declaration by Hattori, Nobuhito, in regard to No. 22056, (yo), served on Dec. 28, 2011. (with English translation).

Unichemy Corp. Experimental Report, in regard to No. 22056, (yo). Issued on Jun. 24, 2011. (with English translation).

Pharmaceutical Additive Dictionary, $2^{nd}$ edition. pp. 153-154, 203-205. Mar. 25, 2002. (with English translation).

Murata, Seishiro. Cosmetic Dictionary, $1^{st}$ edition. pp. 182-183, 666-667. Dec. 15, 2003. (with English translation).

Miyagi, Takashi. Food and Container, vol. 35, No. 10. pp. 588-593. 1994. (with English translation).

Miyagi, Takashi. Food and Container, vol. 35, No. 11. pp. 624-627. 1994. (with English translation).

\* cited by examiner

HAIR COSMETIC PRODUCT

FIELD OF THE INVENTION

The present invention relates to a hair bleach or hair dye cosmetic product in the form of foam.

BACKGROUND OF THE INVENTION

Conventionally, liquid or cream form agents have been widely used as hair cosmetics such as hair bleaches and hair dyes, but it is difficult to apply these types of hair cosmetics uniformly to the hair. In particular, special skills such as "blocking" or a "two mirror technique" are required to apply the cosmetic to the root of the hair or to the back of the head, and a lot of time is also required to do this.

As a countermeasure for such problems, it has been proposed to simplify the hair dyeing operations by discharging agents in the form of foam. For example, such agents include aerosol type hair dyes in which two agents constituting a two agent type hair dye are discharged in foam form from a discharge vessel of the type in which two aerosol cans are connected (see Japanese Patent Application Laid-Open No. 10-287534) and non-aerosol type agents in which a single agent type hair bleach is discharged from a foamer vessel such as a pump foamer or the like as a foam (see Japanese Patent Application Laid-Open No. 9-227347).

However, in the case of agents using a discharge vessel of the type in which two aerosol cans are connected, the first and second agents are each independently discharged from the aerosol cans; accordingly, irregular mixing of the agents tends to occur, so that there may be instances of irregular bleaching (in other words, discoloration) or non-uniform dyeing. Furthermore, since pressure-resistant vessels and caps made of metal are used in the case of aerosol type discharge vessels, these parts are oxidized and corroded by hydrogen peroxide contained in hair bleaches or hair dyes, and there is a danger that the internal pressure inside such pressure-resistant vessels may rise to an excessive pressure and result in the decomposition of this hydrogen peroxide.

On the other hand, in the case of products in which a foamer vessel is filled with a single agent type hair bleach, this hair bleach is applied to the hair without activating hydrogen peroxide, so that the effect obtained in a single application is insufficient. Accordingly, in order to achieve a sufficiently clear bleaching, this hair bleach must be allowed to stand for a considerable period of time following application (e.g., applied in the morning and rinsed away in the evening or the like), and several applications must be repeated, so that the use of such hair bleaches is complicated. As a result, problems also arise in terms of stickiness of the hair while, for example, the hair bleach is allowed to stand.

SUMMARY OF THE INVENTION

The present invention provides a hair cosmetic product containing:

a two agent type hair cosmetic which has a first agent containing an alkali agent and a second agent containing hydrogen peroxide, wherein at least one of the first and second agents contains a surfactant; and a foamer vessel which discharges a mixed liquid comprising the first and second agents in the form of foam. The present invention provides also a hair cosmetic product containing:

a two agent type hair cosmetic which has a first agent containing an alkali agent and a second agent containing hydrogen peroxide, and wherein the first and second agents are mixed immediately prior to use; and a foamer vessel which discharges a mixed liquid containing the first and second agents in the form of foam, wherein the mixed liquid contains a surfactant at an amount of 0.1 to 10 wt %, by weight of the mixed liquid, and the viscosity of the mixed liquid at 25° C. is 1 to 300 mPa·s. Furthermore, the present invention provides a hair treatment method in which a mixed liquid of the first and second agents of the abovementioned hair cosmetic product is applied to the hair by being discharged from a foamer vessel, allowed to stand for 3 to 60 minutes, and then rinsed away.

DETAILED DESCRIPTION OF THE INVENTION

The present invention will be described in detail below.

The present invention has advantages such as to prevent irregular bleaching or non-uniform dyeing in a hair cosmetic product, and also allow a sufficient bleaching power or dyeing power to be obtained, by discharging a hair bleach or hair dye in foam form from a non-aerosol type foamer vessel.

In particular, the preferred embodiments of the present invention provides an aspect in which the first agent contains no dye, this hair cosmetic product being used for hair bleaching, and a second aspect in which the first agent contains an oxidation dye or direct dye, this hair cosmetic product being used for hair dyeing.

If this hair cosmetic product is used, since the first agent contains an alkali agent, the product is superior in terms of hair bleaching power or dyeing power, and a specified hair bleaching effect or dyeing effect can be obtained in a short period of time.

Furthermore, since the first and second agents are discharged after being pre-mixed using a foamer vessel, there is uniform mixing of the first and second agents. Moreover, the mixed liquid that is discharged in the form of foam by gas-liquid mixing using the foamer vessel can easily reach the roots of the hair; however, there is no accumulation of liquid or the like in this area, and the liquid spreads throughout the hair in an appropriately thin layer. Accordingly, unlike a case of using conventional liquid or cream form hair cosmetic products, roots of the hair will not be extremely bright, and also there will be no irregular bleaching or non-uniform dyeing due to unevenness in the amount of mixed liquid that is applied. Accordingly, any difference in color between areas of new growth and areas already dyed can be eliminated, so that a natural finish is obtained, by applying the mixed liquid that is discharged in foam form in the present invention in the vicinity of areas of new growth such as part line, hairline or the like. Furthermore, since the mixed liquid can be applied to the hair as an appropriately thin layer, damage to the hair can be reduced.

Furthermore, in the preferred embodiments of the present invention, since a non-aerosol type vessel can be used as the foamer vessel, the problems of corrosion of the vessel and a rise in internal pressure are also substantially eliminated.

The hair cosmetic product of the present invention contains a two agent type hair cosmetic which has a first agent containing an alkali agent and a second agent containing hydrogen peroxide, wherein at least one of the first and second agents contains a surfactant; and a foamer vessel which discharges a mixed liquid comprising the first and second agents in the form of foam.

The hair cosmetic product of the present invention also contains a two agent type hair cosmetic which has a first agent that contains an alkali agent, and a second agent that contains hydrogen peroxide, and which uses the first and second agents after mixing these agents immediately prior to use, and a foamer vessel which discharges a mixed liquid containing the first and second agents in the form of foam. This hair cosmetic product contains a surfactant at an amount of 0.1 to 10 wt % by weight of the mixed liquid, and the viscosity of the mixed liquid at 25° C. is 1 to 300 mPa·s.

Here, for example, ammonia, alkanolamines such as monoethanolamine or the like, sodium hydroxide, potassium hydroxide or the like can be used as the alkali agent contained in the first agent. Furthermore, ammonium salts such as ammonium hydrogencarbonate, ammonium chloride or the like, or carbonates such as potassium carbonate, sodium hydrogencarbonate or the like, can be added as buffering agents.

The concentration of the alkali agent is appropriately set so that the pH in the mixed liquid of the first and second agents is preferably 8 to 11, more preferably 9 to 11.

Meanwhile, the second agent contains hydrogen peroxide. The concentration of hydrogen peroxide in the second agent is preferably 1 to 9 wt %, and is more preferably 3 to 6 wt %. In the mixed liquid of the first and second agents, this concentration is preferably 1 to 6 wt %, and is more preferably 2 to 5 wt %. Furthermore, in order to suppress decomposition of the hydrogen peroxide, the pH of the second agent is preferably pH 2 to 6, and is more preferably pH 2.5 to 4.

The mixed liquid of the first and second agents contains water as an essential component in a preferred amount constituting the balance of the liquid.

The abovementioned surfactant is contained in the first agent or second agent so that a foam is easily formed by the mixing of air and the hair cosmetic in the foam discharge means of the foamer vessel, and so that this foam is stabilized. Furthermore, in cases where the first agent contains an oxidation dye or direct dye, the surfactant also acts as a solubilizing agent for such dyes. Universally known surfactants can be used as this surfactant. For example, anionic surfactants such as alkylsulfates, polyoxyethylene alkyl ether sulfates or the like, cationic surfactants such as alkyltrimethylammonium chlorides, dialkyldimethylammonium chlorides or the like, amphoteric surfactants such as fatty acid amide propylbetaines, alkyldimethylamine oxides, alkylcarboxymethylhydroxyethylimidazolium betaines, betaine alkyldimethylaminoacetates, sulfobetaine or the like, or nonionic surfactants such as polyoxyethylene alkyl ethers, alkylpolyglycosides, alkylalkanolamides or the like, can be used singly or in mixtures.

In regard to surfactants that are contained mainly in the first agent in order to solubilize oxidation dyes or direct dyes, since the first agent usually contains ammonia or a carbonate, and has a high ionic strength, it is preferable to use nonionic surfactants. In particular, alkylpolyglycosides or polyoxyethylene alkyl ethers are more preferable for use. Alkylpolyglycosides in which the number of carbon atoms in the alkyl group is 10 to 14, and the average degree of glycoside condensation is 1 to 2, may be cited as examples of preferable alkylpolyglycosides. Furthermore, polyoxyethylene alkyl ethers in which the number of carbon atoms in the alkyl group is 10 to 14, and the degree of polymerization of the polyoxyethylene is 10 to 30, may be cited as examples of more preferable polyoxyethylene alkyl ethers.

Furthermore, in order to realize good foaming that allow easy application to the hair, it is preferable to use an anionic surfactant as the surfactant. Preferred anionic surfactants include polyoxyethylene alkyl ether sulfates, and preferably sodium polyoxyethylene lauryl ether sulfates. Furthermore, the combined use of amphoteric surfactants such as fatty acid amide propylbetaines, sulfobetaine or the like with such anionic surfactants is more preferable. Such anionic surfactants or amphoteric surfactants are contained in the first agent or second agent; however, in view of the fact that the first agent usually contains ammonia or a carbonate, and has a high ionic strength, it is preferable that such surfactants be contained in the second agent.

In order to obtain good foaming that allows easy application to the hair, and in order to obtain good foam stability, the surfactant content in the mixed liquid of the first and second agents is 0.1 to 10 wt %. Furthermore, a preferred content in the aspect of the present invention used for hair bleaching is 0.1 to 3 wt %; in this case, a content of 0.5 to 2.5 wt % is more preferable, and a content of 1 to 2 wt % is even more preferable. Furthermore, in the aspect of the present invention used for hair dyeing, since solubilizing the oxidation dye or direct dye may be necessary, a preferable content is 1 to 5 wt %, and a content of 2 to 4 wt % is more preferable.

In cases where no dye is contained in the hair cosmetic, the hair cosmetic product of the present invention can be used for hair bleaching; this hair cosmetic product can be used for hair dyeing by including an oxidation dye or direct dye. In cases where the hair cosmetic product is used for hair dyeing, the first agent contains an oxidation dye or direct dye. Examples of such oxidation dyes include dye precursors such as para-phenylenediamine, para-aminophenol, toluene-2,5-diamine, N,N-bis(2-hydroxyethyl)paraphenylenediamine, 2-(2-hydroxyethyl)paraphenylenediamine, 4-amino-3-methylphenol, 6-amino-3-methylphenol, ortho-aminophenol, 1-hydroxyethyl-4,5-diaminopyrazole and the like, and couplers such as resorcine, 2-methylresorcine, meta-aminophenol, para-amino-ortho-cresol, 5-(2-hydroxyethylamino)-2-methylphenol, meta-phenylenediamine, 2,4-diaminophenoxyethanol, 1-naphthol and the like. Examples of direct dyes include para-nitro-ortho-phenylenediamine, para-nitro-meta-phenylenediamine, basic yellow 87, basic orange 31, basic red 12, basic red 51, basic blue 99, acid orange 7 and the like.

Furthermore, in the present invention, it is preferable that the first or second agent, and more preferably the second agent, contain a nonvolatile hydrophilic solvent in a relatively large amount. As a result, the irritation of the scalp caused by the concentration of irritating components such as hydrogen peroxide or the like due to the evaporation of moisture from the hair cosmetic while the cosmetic is being allowed to stand after the two agent type hair cosmetic has been applied to the hair can be alleviated. It is preferable that a solvent that has no defoaming action be used as such a nonvolatile hydrophilic solvent. Examples of such solvents include polyols and lower alkyl ethers of the same. Polyols with 2 to 6 carbon atoms are preferable. Examples of such polyols include glycerol, propylene glycol, dipropylene glycol, 1,3-butanediol, ethylene glycol, diethylene glycol, isoprene glycol, sorbitol and the like. Examples of lower alkyl ethers of polyols include mono-lower alkyl ethers and poly-lower alkyl ethers (e.g., di-lower alkyl ethers) of the abovementioned polyols. In particular, monomethyl ethers or monoethyl ethers of polyols are preferable, and ethylene glycol monomethyl ether, ethylene glycol monoethyl ether, diethylene glycol monomethyl ether and diethylene glycol monoethyl ether are more preferable.

From the standpoint of reducing scalp irritation and obtaining good foam quality, it is preferable that the content of the nonvolatile hydrophilic solvent be set at 0.1 to 30 wt % in the mixed liquid of the first and second agents. A content of 5 to 30 wt % is more preferable, a content of 10 to 30 wt % is even more preferable, and a content of 12 to 25 wt % is even more preferable.

Furthermore, in the present invention, it is preferable that the first or second agent contains a higher alcohol. Foam retention is improved by such a higher alcohol, and this is effective in preventing the dripping of liquid while the two agent type cosmetic is being allowed to stand following application to the hair. Compounds with 10 to 24 carbon atoms are preferable as higher alcohols; examples of such higher alcohols include lauryl alcohol, cetyl alcohol, stearyl alcohol, isostearyl alcohol, oleyl alcohol and the like. Two or more of these alcohols can be used in combination.

From the standpoint of controlling liquid dripping and improving the foam quality, it is preferable that the content of the abovementioned higher alcohol be set at 0.1 to 3 wt % by weight of the mixed liquid of the first and second agent; a content of 0.2 to 2 wt % is more preferable, and a content of 0.3 to 1.5 wt % is even more preferable.

Furthermore, in the present invention, it is preferable that the first or second agent contains a cationic polymer. A conditioning effect can be imparted to the hair by such a cationic polymer. In cases where a cationic polymer is added, it is preferable to cause this polymer to form a complex with an anionic surfactant in order to improve the tactile sensation during rinsing. However, from the standpoint of storage stability, it is preferable that this polymer be added to the first agent separately from the second agent, which contains an anionic surfactant. The cationic polymer is preferably contained in the mixed liquid of the first and second agents at an amount of 0.1 to 3 wt %, and more preferably at an amount of 0.1 to 1 wt %.

Here, the term "cationic polymer" refers to a polymer which has cationic groups or groups that can be ionized into cationic groups. This term includes amphoteric polymers that are cationic on the whole. Specifically, examples of cationic polymers include polymers in aqueous solution that contain amino groups or ammonium groups in the side chains of the polymer chains, or that contain diallyl quaternary ammonium salts as constituent units, e.g., cationized cellulose derivatives, cationic starches, cationized guar gum derivatives, polymers or copolymers of diallyl quaternary ammonium salts, quaternized polyvinylpyrrolidone derivatives and the like. Among these compounds, polymers that include diallyl quaternary ammonium salts as constituent units, quaternized polyvinylpyrrolidone derivatives and cationized cellulose derivatives are preferable from the standpoints of softness and smoothness of tactile sensation during rinsing and shampooing, ability to pass the fingers through, ease of arrangement during drying, moisture retention and storage stability; from these standpoints, polymers or copolymers of diallyl quaternary ammonium salts and cationized cellulose derivatives are preferable, and polymers or copolymers of diallyl quaternary ammonium salts are more preferable.

The skeletons indicated by the following general formula (1) or (2) are preferable as the skeletons of such polymers of diallyl quaternary ammonium salts.

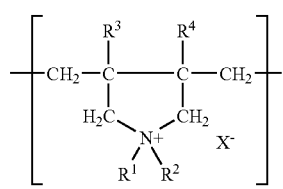

(1)

-continued

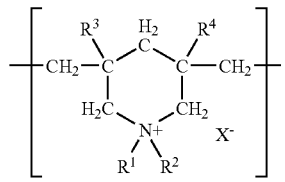

(2)

In formulae (1) and (2), $R^1$ and $R^2$ may be the same or different, and indicate hydrogen atoms, alkyl groups with 1 to 18 carbon atoms, aryl groups (phenyl groups or the like), hydroxyalkyl groups, amidoalkyl groups, cyanoalkyl groups, alkoxyalkyl groups or carboalkoxyalkyl groups. $R^3$ and $R^4$ may be the same or different, and indicate hydrogen atoms, alkyl groups with 1 to 3 carbon atoms or phenyl groups. $X^-$ indicates an anion (chloride ion, bromide ion, iodide ion, sulfuric acid anion, sulfonic acid anion, methylsulfuric acid anion, phosphoric acid anion, nitric acid anion or the like).

Examples of monomers that may constitute a copolymer with diallyl quaternary ammonium salts include acrylic acid, methacrylic acid or salts or acrylamides of these acids. In particular, acrylic acid, methacrylic acid or salts of these acids are preferable. Copolymers of acrylic acid, methacrylic acid or salts of these acids with diallyl quaternary ammonium salts have a high constituent ratio of diallyl quaternary ammonium salts, and are cationic polymers overall.

Concrete examples of polymers or copolymers of diallyl quaternary ammonium salts include dimethyldiallylammonium chloride polymers (Polyquaternium-6, e.g., Mercoat 100; ONDEO Nalco Co.), dimethyldiallylammonium chloride/acrylic acid copolymers (Polyquaternium-22, e.g., Mercoat 280 and 295; ONDEO Nalco Co.), dimethyldiallylammonium chloride/acrylamide copolymers (Polyquaternium-7, e.g., Mercoat 550; ONDEO Nalco Co.) and the like. In particular, Mercoat 280 and 295 are preferred.

Compounds expressed by the following general formula (3) are preferable as quaternized polyvinylpyrrolidone derivatives.

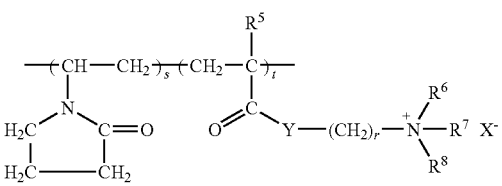

(3)

In formula (3), $R^5$ indicates a hydrogen atom or an alkyl group with 1 to 3 carbon atoms, $R^6$, $R^7$ and $R^8$ may be the same or different, and indicate hydrogen atoms, alkyl groups with 1 to 4 carbon atoms, hydroxyalkyl groups, amidoalkyl groups, alkoxyalkyl groups or carboalkoxyalkyl groups, Y indicates an oxygen atom or an imino group, r indicates an integer of 1 to 10, the total of s and t indicates a number from 20 to 8,000, and $X^-$ has the same meaning as described above.

It is preferable that the molecular weight of the quaternized polyvinylpyrrolidone derivatives used in the present invention be 10,000 to 2,000,000, and a molecular weight of 50,000 to 1,500,000 is more preferable. Examples of commercially marketed products include Gafcoat 734, 755 and 755N (ISP Japan Co.).

For example, compounds expressed by the following general formula (4) are preferable as cationized cellulose derivatives.

In formula (4), A indicates the residue of an anhydroglucose unit, f indicates an integer from 50 to 20,000, and each $R^9$ indicates a substituent group expressed by the following general formula (5).

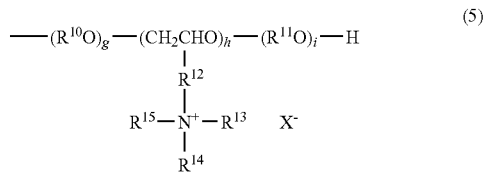

In formula (5), $R^{10}$ and $R^{11}$ indicate alkylene groups with 2 or 3 carbon atoms, g indicates an integer from 0 to 10, h indicates an integer from 0 to 3, i indicates an integer from 0 to 10, $R^{12}$ indicates an alkylene group or a hydroxyalkylene group with 1 to 3 carbon atoms, and $R^{13}$, $R^{14}$ and $R^{15}$ may be the same or different, and indicate alkyl groups, aryl groups or aralkyl groups with up to 10 carbon atoms; furthermore, these groups may form a hetero-ring containing a nitrogen atom in the formula. $X^-$ has the same meaning as described above.

It is preferable that the degree of cation substitution of such cationized cellulose derivatives, i.e., the mean value of h per anhydroglucose unit, be 0.01 to 1, and a value of 0.02 to 0.5 is more preferable. Furthermore, the total of g+i is 1 to 3. In cases where the degree of cation substitution is less than 0.01, this degree of substitution is insufficient. On the other hand, although this value may exceed 1, from the standpoint of the reaction yield, it is preferable that this value be 1 or less. It is preferable that the molecular weight of cationized cellulose derivatives used here be 100,000 to 3,000,000. Examples of commercially marketed products include Leogard G and GP (Lion Co.), Polymer JR-125, JR-400, JR-30M, LR-400 and LR-30M (Union Carbide Co.) and the like. Examples of other cationized cellulose derivatives that can be used include hydroxyethylcellulose dimethyldiallylammonium chloride; examples of commercially marketed products of this type include Celcoat H-100 and L-200 (National Starch and Chemical Co.).

If necessary, furthermore, the first or second agent may contain fragrances, ultraviolet absorbing agents, metal blocking agents such as edetic acid or the like, microbicidal agents, preservatives such as methyl para-oxybenzoate or the like, stabilizing agents such as phenacetin, 1-hydroxyethane-1,1-diphosphonic acid or the like, volatile or hydrophobic solvents such as ethanol, benzyl alcohol or the like, water-soluble macromolecular compounds such as hydroxyethylcellulose or the like, silicones such as dimethylpolysiloxane, polyether-modified silicone, amodimethicone or the like, moisture-retaining agents or the like.

Furthermore, the first and second agent are prepared so that the viscosity of the mixed liquid of these agents (taken as the value obtained following rotation for 1 minute at 30 rpm using a No. 1 rotor in a B type rotary viscometer at 25° C.; if the viscosity exceeds 160 mPa·s, taken as the value similarly obtained following rotation for 1 minute at 12 rpm) is preferably 50 mPa·s or less, more preferably 10 mPa·s or less. If the viscosity is adjusted to a value in this range, a foam volume (i.e., gas-liquid mixture ratio) that allows easy application can be realized regardless of the temperature; accordingly, such a viscosity is preferable. Furthermore, the first and second agent are prepared so that the viscosity of the mixed liquid of these agents is 1 to 300 mPa·s at 25° C., preferably 10 to 200 mPa·s, and more preferably 30 to 120 mPa·s. If the viscosity is adjusted to a value in this range, a foam volume that allows easy application can be realized regardless of the temperature and drops of the mixed liquid can be prevented from falling down between when applying the mixed liquid to the hair and when allowing the applied mixed liquid to stand on the hair; accordingly, such a viscosity is effective. Here, from the standpoints of good affinity of the agents for the hair and ease of application, it is preferable that the gas-liquid mixture ratio be 7 to 40 mL/g, and a ratio of 15 to 30 mL/g is more preferable. Furthermore, the gas-liquid mixture ratio referred to here is a value which can be measured as follows.

First, the gas-liquid mixture ratio is determined by measuring the weight and volume of the foam that is discharged at 25° C. For example 100 g of a mixed liquid is placed in the bottle of a squeeze foamer vessel (manufactured by Yamato Seikan K.K., volume: 150 mL, mesh coarseness (openings): 200 mesh in the mixing compartment (200 measures per inch (25.4 mm)), 255 mesh at the tip end). 20 g of foam is discharged into a 100-mL graduated cylinder from the point in time at which the residue reaches 80 g, and the volume of foam is measured 1 minute following the initial discharge. The gas-liquid mixture ratio (mL/g) is obtained by dividing this volume (mL) of the discharged foam by a weight of 20 g.

Furthermore, adjustment of the viscosity of the mixed liquid to a value in the abovementioned range is preferable, since this facilitates squeezing when the foam is discharged by a squeeze foamer or the like. A water-soluble solvent such as ethanol or the like may be added, or the contents and types of the surfactant, polyol and higher alcohol may be appropriately adjusted, in order to adjust the viscosity of the mixed liquid of the first and second agent to a value in the abovementioned range.

Furthermore, it is preferable that the first and second agents have a liquid form; however, as long as these agents form a solution in which the viscosity of the mixed liquid of the first and second agents is 1 to 300 mPa·s at 25° C., the first agent or second agent may have the form of a powder, granules, paste or the like.

In addition, a persulfate such as ammonium persulfate or the like may be contained in the mixed liquid in order to heighten the hair bleaching effect.

In the present invention, the foamer vessel is a non-aerosol type vessel which is used to mix the mixed liquid of the first and second agents with air and to discharge this mixture in the form of foam without using a propellant. As a result of the use of such a foamer vessel, scattering of the discharged agents can also be prevented. In particular, as compared with an aerosol type vessel, such a non-aerosol type vessel can be manufactured at a lower cost, and does not require any high-pressure gas as a propellant, whereby hair cosmetic products using such a non-aerosol type vessel can be handled more safely in the distribution step.

Universally known pump foamer vessels, squeeze foamer vessels, electric foam generators, cumulative pressure type foamer vessels or the like that have foam discharge means can be used as the abovementioned foamer vessel. Concrete examples of such vessels include the pump foamer E3 type and F2 type (manufactured by Yamato Seikan K.K.), squeeze foamer (manufactured by Yamato Seikan K.K.), electric foam generator (manufactured by Matushita Denko), air spray foamer (manufactured by Air Spray International Co.) and the like described in *Shokuhin to Yoki* [Food Products and Containers] (Vol. 35, No. 10, pp. 588-593 (1994); Vol. 35, No. 11, pp. 624-627 (1994); Vol. 36, No. 3, pp. 154-158 (1995)).

In such a foamer vessel, it is preferable that the portions that contact the contents (inside walls of the vessel, inside walls of the foam discharge means and the like) be constructed from materials that are not corroded by alkali agents or hydrogen peroxide, and that allow oxygen generated by the decomposition of hydrogen peroxide to pass through.

In regard to the product configuration of the hair cosmetic product of the present invention containing the abovementioned first agent, second agent and foamer vessel, this configuration may be devised so that containers that are separate from the foamer vessel are respectively filled with the first agent or second agent, and both agents are transferred into the foamer vessel at the time of use; on the other hand, this product configuration may also be devised so that the foamer vessel is filled with one agent, a separate container is filled with the other agent, and this other agent is transferred into the foamer vessel at the time of use. In this case, it is preferable that the second agent be placed in a container that has gas permeability in order to prevent a rise in the internal pressure of the container caused by oxygen generated by the decomposition of the hydrogen peroxide. On the other hand, in the case of the first agent, it is necessary to use a container resistant to oxygen permeation in order to prevent oxidation of the oxidation dye and volatilization of the ammonia. Accordingly, it is preferable that the second agent be placed in a foamer vessel constructed from a material with oxygen permeability (e.g., polyethylene).

Furthermore, in regard to the method of use of the hair cosmetic product of the present invention, the foam form agents discharged from the foamer vessel following the mixing of the first and second agents inside this vessel may be applied directly to the hair, or may be applied to the hair using the hands or an implement such as a brush or the like. The applied preparation is allowed to stand for approximately 3 to 60 minutes, preferably approximately 5 to 45 minutes, following application, and is then rinsed away. Preferably subsequently, following appropriate shampooing or rinsing, rinsing is performed with water, and the hair is then dried.

The present invention provides a hair cosmetic product containing:

a two agent type hair cosmetic which has a first agent containing an alkali agent and a second agent containing hydrogen peroxide, wherein at least one of the first and second agents contains a foaming agent; and a foamer vessel which discharges a mixed liquid comprising the first and second agents in the form of foam.

In particular, the preferred embodiments of the present invention provides an aspect in which the first agent contains no dye, this hair cosmetic product being used for hair bleaching, and a second aspect in which the first agent contains an oxidation dye or direct dye, this hair cosmetic product being used for hair dyeing.

Furthermore, the present invention provides a hair treatment method in which a mixed liquid of the first and the second agents of the abovementioned hair cosmetic product is applied to the hair by being discharged from a foamer vessel, allowed to stand for 3 to 60 minutes, and then rinsed away.

If this hair cosmetic product is used, since the first agent contains an alkali agent, the product is superior in terms of hair bleaching power or dyeing power, and a specified hair bleaching effect or dyeing effect can be obtained in a short period of time.

Furthermore, since the first and second agents are discharged after being pre-mixed using a foamer vessel, there is uniform mixing of the first and second agents. Moreover, the mixed liquid that is discharged in the form of foam by gas-liquid mixing using the foamer vessel can easily reach the roots of the hair; however, there is no accumulation of liquid or the like in this area, and the liquid spreads throughout the hair in an appropriately thin layer. Accordingly, unlike a case of using conventional liquid or cream form hair cosmetic products, roots of the hair will not be extremely bright, and also there will be no irregular bleaching or non-uniform dyeing due to unevenness in the amount of mixed liquid that is applied. Accordingly, any difference in color between areas of new growth and areas already dyed can be eliminated, so that a natural finish is obtained, by applying the mixed liquid that is discharged in foam form in the present invention in the vicinity of areas of new growth such as part line, hairline or the like. Furthermore, since the mixed liquid can be applied to the hair as an appropriately thin layer, damage to the hair can be reduced.

Furthermore, in the preferred embodiments of the present invention, since a non-aerosol type vessel can be used as the foamer vessel, the problems of corrosion of the vessel and a rise in internal pressure are also substantially eliminated.

The present invention will be described in detail below. The hair cosmetic product of the present invention comprises a first agent containing an alkali agent and a second agent containing hydrogen peroxide and a foamer vessel, and at least one of the first and second agents contains a foaming agent.

Here, for example, ammonia, monoethanolamine or the like can be used as the alkali agent contained in the first agent, and ammonium salts such as ammonium hydrogencarbonate, ammonium chloride or the like and hydrogen carbonate can be added as buffering agents.

The concentration of the alkali agent is appropriately set so that the pH in the mixed liquid of the first and second agents is preferably 8 to 11, more preferably 9 to 11.

A foaming agent is compounded into the first agent or second agent so that a foam is easily formed by the mixing of air and the hair cosmetic in the foam discharge means of the foamer vessel, and so that this foam is stabilized. As this foaming agent, universally known foaming agents can be used. For example, anionic surfactants such as alkylsulfates, polyoxyethylene alkyl ether sulfates or the like, cationic surfactants such as alkyltrimethylammonium chlorides, dialkyldimethylammonium chlorides or the like, amphoteric surfactants such as fatty acid amide propylbetaines, alkyldimethylamine oxides, alkylcarboxymethylhydroxyethylimidazolium betaines, betaine alkyldimethylaminoacetates, sulfobetaine or the like, or nonionic surfactants such as polyoxyethylene alkyl ethers, alkylalkanolamides or the like, can be used singly or in mixtures. Among them, in order to fulfill good foaming, anionic surfactants which contains alkyl group or acyl group with 12 carbon atoms is preferable as a foaming agent. In particular, sodium polyoxyethylene lauryl ether sulfate is preferable.

In order to obtain good foaming and good foam stability, the foaming agent content in the mixed liquid of the first and second agents preferably be 0.1 to 3 wt %, a content of 0.5 to 2.5 wt % is more preferable, and a content of 1 to 2 wt % is even more preferable.

In cases where no dye is contained in the hair cosmetic, the hair cosmetic product of the present invention can be used for hair bleaching; this hair cosmetic product can be used for hair dyeing by including an oxidation dye or direct dye. In cases where the hair cosmetic product is used for hair dyeing, the first agent contains an oxidation dye or direct dye. Examples of such oxidation dyes include dye precursors such as par-aphenylenediamine, para-aminophenol, toluene-2,5-diamine, ortho-aminophenol and the like, and couplers such as resorcine, meta-aminophenol, para-aminoorthocresol, meta-phenylenediamine, and the like. Examples of direct dyes include para-nitro-ortho-phenylenediamine, para-nitro-meta-phenylenediamine sulfate, basic yellow 87, and the like.

Furthermore, in order to obtain good bleaching effect, persulfate such as ammonium persulfate or the like can be used if necessary.

On the other hand, the second agent contains hydrogen peroxide. The concentration of the hydrogen peroxide preferably be 1 to 9 wt %, more preferably 3 to 6 wt %. Moreover, from the standpoint of controlling the decomposition of the hydrogen peroxide, the pH of the second agent preferably be pH 2 to 6, and pH 2.5 to 4 is more preferable.

Furthermore, in the present invention, it is preferable that the first or second agent, and more preferably the second agent, contain a nonvolatile hydrophilic solvent in a relatively large amount. As a result, the irritation of the scalp caused by the concentration of irritating components such as hydrogen peroxide or the like due to the evaporation of moisture from the hair cosmetic while the cosmetic is being allowed to stand after the two agent type hair cosmetic has been applied to the hair can be alleviated. It is preferable that a solvent that has no defoaming action be used as such a nonvolatile hydrophilic solvent. Examples of such solvents include polyols with 2 to 6 carbon atoms such as glycerol, propylene glycol, and the like, and among them, from the standpoint of good foaming, glycerol is preferable.

From the standpoint of obtaining good foam quality, it is preferable that the content of the nonvolatile hydrophilic solvent be set at 5 to 30 wt % in the mixed liquid of the first and second agents. A content of 10 to 30 wt % is more preferable, a content of 15 to 25 wt % is even more preferable.

If necessary, furthermore, the first or second agent may contain fragrances, ultraviolet absorbing agents, metal blocking agents, microbicidal agents, preservatives, volatilehydrophilic solvents such as ethanol or the like, water, water-soluble macromolecular compounds, moisture-retaining agents or the like.

Furthermore, the first and the second agent are prepared so that the viscosity of the mixed liquid of these agents is preferably 50 mPa·s or less, more preferably 10 mPa·s or less at 25° C. If the viscosity is adjusted to a value in this range, a foam volume (i.e., gas-liquid mixture ratio) that allows easy application can be realized regardless of the temperature; accordingly, such a viscosity is preferable. Here, from the standpoints of good affinity of the agents for the hair and ease of application, it is preferable that the gas-liquid mixture ratio be 7 to 40 mL/g, and a ratio of 15 to 30 mL/g is more preferable.

Furthermore, adjustment of the viscosity of the mixed liquid to a value in the abovementioned range is preferable, since this facilitates squeezing when the foam is discharged by a squeeze foamer or the like. A water-soluble solvent such as ethanol or propylene glycol or the like may be added, or the contents and types of foaming agents, and polyol may be appropriately adjusted, in order to adjust the viscosity of the mixed liquid of the first and the second agent to a value in the abovementioned range.

In the present invention, the foamer vessel is used to mix the mixed liquid of the first and the second agents with air and to discharge this mixture in the form of foam without using a propellant. As a result of the use of such a foamer vessel, scattering of the discharged agents can also be prevented.

Universally known pump foamer vessels, squeeze foamer vessels, electric foam generators, cumulative pressure type foamer vessels or the like that have foam discharge means can be used as the abovementioned foamer vessel. Concrete examples of such vessels include the pump foamer E3 type and F2 type (manufactured by Yamato Seikan K.K.), squeeze foamer (manufactured by Yamato Seikan K.K.), electric foam generator (manufactured by Matushita Denko), air spray foamer (manufactured by Air Spray International Co.) and the like described in *Shokuhin to Yoki* [Food Products and Containers] (Vol. 35, No. 10, pp. 588-593 (1994); Vol. 35, No. 11, pp. 624-627 (1994); Vol. 36, No. 3, pp. 154-158 (1995)).

In such a foamer vessel, it is preferable that the portions that contact the contents (inside walls of the vessel, inside walls of the foam discharge means and the like) be constructed from materials that are not corroded by alkali agents or hydrogen peroxide, and that allow oxygen generated by the decomposition of hydrogen peroxide to pass through.

In regard to the product configuration of the hair cosmetic product of the present invention containing the abovementioned first agent, second agent and foamer vessel, this configuration may be devised so that containers that are separate from the foamer vessel are respectively filled with the first agent or second agent, and both agents are transferred into the foamer vessel at the time of use; on the other hand, this product configuration may also be devised so that the foamer vessel is filled with one agent, a separate container is filled with the other agent, and this other agent is transferred into the foamer vessel at the time of use. In this case, it is preferable that the second agent be placed in a container that has gas permeability in order to prevent a rise in the internal pressure of the container caused by oxygen generated by the decomposition of the hydrogen peroxide. On the other hand, in the case of the first agent, it is necessary to use a container resistant to oxygen permeation in order to prevent oxidation of the oxidation dye and volatilization of the ammonia. Accordingly, it is preferable that the second agent be placed in a foamer vessel constructed from a material with oxygen permeability (e.g., polyethylene).

Furthermore, in regard to the method of use of the hair cosmetic product of the present invention, the foam form agents discharged from the foamer vessel following the mixing of the first and second agents inside this vessel may be applied directly to the hair, or may be applied to the hair using the hands or an implement such as a brush or the like. The applied preparation is allowed to stand for approximately 3 to 60 minutes, preferably approximately 5 to 45 minutes, following application, and is then rinsed away. Preferably subsequently, following appropriate shampooing or rinsing, rinsing is performed with water, and the hair is then dried.

The following examples further describe and demonstrate embodiments of the present invention. The examples are given solely for the purpose of illustration and are not to be construed as limitations of the present invention.

EXAMPLES

Examples 1A Through 1C

Cosmetic Products for Hair Bleaching

A first agent and second agent are prepared using the compositions shown in Table 1, and the first agent and second agent are placed in (A) a squeeze foamer (manufactured by Yamato Seikan K.K.), (B) a pump foamer (F2 type, manufactured by Yamato Seikan K.K.) or (C) an electric foam generator (Awawash, manufactured by Matsushita Denko), and mixed at a mixture ratio (weight ratio) of 1:1.5, after which the mixed liquid is discharged. 80 g of the discharged foam is applied to the hair as a whole; hair bleaching is accomplished by allowing this foam to stand for 30 minutes, and then rinsing the foam away. In this case, foaming, foam duration, irritation of the scalp, irregular hair bleaching, coating properties (ease of coating, affinity for the hair) and scattering of the agents are respectively evaluated using the criteria shown below. The results are shown in Table 2.

TABLE 1

| First agent | Concentration in first agent (wt %) |
|---|---|
| Strong aqueous ammonia (28%) | 8.0 |
| Ammonium hydrogencarbonate | 14.0 |
| Methyl para-oxybenzoate | 0.1 |
| Fragrance | 0.5 |
| Water | balance |

| Second agent | Concentration in second agent (wt %) |
|---|---|
| Sodium polyoxyethylene (2.5) lauryl ether sulfate | 1.9 |
| Lauric acid amide propylbetaine | 0.05 |
| Laurylhydroxysulfobetaine | 0.05 |
| Lauric acid | 0.04 |
| Phosphoric acid (75%) | Amount required to adjust second agent to pH 3.8 |
| Glycerol | 30.0 |
| Hydrogen peroxide (35%) | 16.3 |
| Water | balance |

Surfactant concentration following mixing: 1.22 wt %
Viscosity: 15 mPa·s
The following evaluation criteria can be applied:
Evaluation Criteria for Foaming
"Superior": Extremely uniform fine foam
"Good": Uniform fine foam
"Normal": Non-uniform coarse foam
"Poor": Foam not formed; moisture admixed.
Evaluation Criteria for Foam Duration
"Superior": Extremely long duration; foam lasted while being allowed to stand.
"Good": Sufficient duration; foam lasted for some time following application.
"Normal": Foam showed sufficient duration so that there was no problem in application; however, foam quickly disappeared following application.
"Poor": Foam disappeared immediately following discharge, and liquid dripping occurred during application.
Evaluation Criteria for Irritation of Scalp
"Superior": No feeling of irritation
"Good": Almost no feeling of irritation
"Normal": Irritation felt, but not at a level that could not be endured.
"Poor": Severe irritation felt.
Evaluation Criteria for Irregular Hair Bleaching
"Superior": Extremely uniform hair bleaching possible without any irregular hair bleaching.
"Good": Uniform hair bleaching possible with hardly any irregular hair bleaching.
"Normal": Slight irregularity in hair bleaching
"Poor": Major irregularity in hair bleaching Evaluation Criteria for Coating Properties (Ease of Application, Affinity for Hair)
"Superior": Agents firmly penetrated to roots merely by pressing the foam on the hair.
"Good": Agents could easily be caused to penetrate to roots by kneading with hands.
"Normal": Cases occurred in which penetration of the agents was difficult depending on location, as in the roots on the back portion of the head where the quantity of hair was large.
"Poor": Poor penetration; failure to coat roots and the like.

TABLE 2

|  | A: Squeeze foamer | B: Pump foamer | C: Electric foam generator |
|---|---|---|---|
| Foaming | Good | Superior | Superior |
| Foam duration | Good | Superior | Superior |
| Irritation of scalp | Good | Good | Good |
| Irregular hair bleaching | Superior | Superior | Superior |
| Coating properties | Good | Superior | Superior |
| Scattering of agents | none | none | none |

It is seen in Table 2 that there is no scattering of the agents, hair bleaching is possible without irregularity, and scalp irritation is not a problem, when any of the foamer vessels A, B and C are used.

Furthermore, in the case of hair with conspicuous differences in color (brightness) between black hair in areas of new growth and bleached hair from which color is removed (as time elapses following the final hair bleaching), this difference is eliminated, so that a natural finish can be obtained, regardless of the foamer vessel that is used.

Example 2

Hair Cosmetic Product for Hair Dyeing

A first agent and second agent are prepared using the compositions shown in Table 3; the first and second agents are placed in a squeeze foamer A and mixed at a mixture ratio (weight ratio) of 1:1.5, and these agents are then discharged in the form of foam. 80 g of the discharged foam is applied to the hair as a whole; hair dyeing is accomplished by allowing this foam to stand for 30 minutes, and then rinsing the foam away. There is no scattering of the agents, hair dyeing is accomplished without irregularity, and scalp irritation is not a problem.

Furthermore, differences in color between black hair in areas of new growth and the color of the hair in already dyed areas is eliminated, so that a natural finish can be obtained.

TABLE 3

| First agent | Concentration in first agent (wt %) |
|---|---|
| Strong aqueous ammonia (28%) | 8.0 |
| Ammonium hydrogencarbonate | 14.0 |
| Methyl para-oxybenzoate | 0.1 |
| Fragrance | 0.5 |
| Ascorbic acid | 0.3 |
| Anhydrous sodium sulfite | 0.4 |

TABLE 3-continued

| | |
|---|---|
| Toluene-2,5-diamine | 0.5 |
| Resorcine | 0.4 |
| Water | balance |

| Second agent | Concentration in second agent (wt %) |
|---|---|
| Sodium polyoxyethylene (2.5) lauryl ether sulfate | 1.9 |
| Lauric acid amide propylbetaine | 0.05 |
| Laurylhydroxysulfobetaine | 0.05 |
| Lauric acid | 0.04 |
| Phosphoric acid (75%) | Amount required to adjust second agent to pH 3.8 |
| Glycerol | 30.0 |
| Hydrogen peroxide (35%) | 16.3 |
| Water | balance |

Concentration of surfactant following mixing: 1.22 wt %
Viscosity: 15 mPa·s

Examples 3 and 4

Hair Cosmetic Products for Hair Dyeing

A first agent and second agent are prepared using the compositions shown in Tables 4 and 5; the first and second agents are placed in a squeeze foamer A and mixed at a mixture ratio (weight ratio) of 1:1.5, and these agents are then discharged in the form of foam. The overall hair is dyed in the same manner as in Example 2 using 80 g of the discharged foam. There is no scattering of the agents, hair dyeing is accomplished without irregularity, and scalp irritation is not a problem.

Furthermore, differences in color between black hair in areas of new growth and the color of the hair in already dyed areas are eliminated, so that a natural finish can be obtained.

TABLE 4

| First agent | Concentration in first agent (wt %) |
|---|---|
| Strong aqueous ammonia (28%) | 8.0 |
| Ammonium hydrogencarbonate | 14.0 |
| Methyl para-oxybenzoate | 0.1 |
| Fragrance | 0.5 |
| Ascorbic acid | 0.3 |
| Anhydrous sodium sulfite | 0.4 |
| Toluene-2,5-diamine | 0.5 |
| Resorcine | 0.4 |
| Sodium polyoxyethylene (2.5) lauryl ether sulfate | 1.9 |
| Lauric acid amide propylbetaine | 0.05 |
| Laurylhydroxysulfobetaine | 0.05 |
| Lauric acid | 0.04 |
| Water | balance |

| Second agent | Concentration in second agent (wt %) |
|---|---|
| Phosphoric acid (75%) | Amount required to adjust second agent to pH 3.8 |
| Glycerol | 30.0 |
| Hydrogen peroxide (35%) | 16.3 |
| Water | balance |

Concentration of surfactant following mixing: 0.82 wt %
Viscosity: 15 mPa·s

TABLE 5

| First agent | Concentration in first agent (wt %) |
|---|---|
| Para-aminophenol | 0.8 |
| Meta-aminophenol | 0.2 |
| Toluene 2,5-diamine | 0.5 |
| Resorcine | 0.6 |
| Strong aqueous ammonia (28%) | 8.5 |
| Ammonium hydrogencarbonate | 8.0 |
| Decylpoly(1.4)glycoside | 3.2 |
| Polyoxyethylene(23)lauryl ether | 2.0 |
| Propylene glycol | 4.0 |
| Dimethyldiallylammonium chloride-acrylic acid copolymer | 0.4 |
| Methyl para-oxybenzoate | 0.1 |
| Tetrasodium edetate dihydrate | 0.1 |
| Fragrance | 0.5 |
| Ascorbic acid | 0.3 |
| Anhydrous sodium sulfite | 0.4 |
| Water | balance |

| Second agent | Concentration in second agent (wt %) |
|---|---|
| Sodium polyoxyethylene (2.5) lauryl ether sulfate | 1.9 |
| Lauric acid amide propylbetaine | 0.05 |
| Laurylhydroxysulfobetaine | 0.05 |
| Lauric acid | 0.04 |
| Cetyl alcohol | 1.5 |
| 1-Hydroxyethane-1,1-diphosphonic acid | 0.04 |
| Phosphoric acid (75%) | Amount required to adjust second agent to pH 3.8 |
| Sodium hydroxide solution (48%) | 0.01 |
| Glycerol | 20.0 |
| Hydrogen peroxide (35%) | 16.3 |
| Water | balance |

Concentration of surfactant following mixing: 3.30 wt %
Viscosity: 80 mPa·s

Examples 5A Through 5C

Cosmetic Products for Hair Bleaching

A first agent and second agent are prepared using the compositions shown in Table 6, and the first agent and second agent are placed in (A) a squeeze foamer (manufactured by Yamato Seikan K.K.), (B) a pump foamer (F2 type, manufactured by Yamato Seikan K.K.) or (C) an electric foam generator (Awawash, manufactured by Matsushita Denko), and mixed at a mixture ratio (weight ratio) of 1.0:1.5, after which the mixed liquid is discharged. 80 g of the discharged foam is applied to the hair as a whole; hair bleaching is accomplished by allowing this foam to stand for 30 minutes, and then rinsing the foam away. In this case, foaming, foam duration, irritation of the scalp, irregular hair bleaching, coating properties (ease of coating, affinity for the hair) and scattering of the agents are respectively evaluated using the criteria shown below. The results are shown in Table 7.

TABLE 6

| First agent | Concentration in first agent (wt %) |
|---|---|
| Strong aqueous ammonia (28%) | 8.0 |

TABLE 6-continued

|  |  |
|---|---|
| Ammonium hydrogencarbonate | 14.0 |
| Methyl para-oxybenzoate | 0.1 |
| Fragrance | 0.5 |
| Purified Water | balance |
| Second agent | Concentration in second agent (wt %) |
| Sodium polyoxyethylene lauryl ether sulfate | 1.4 |
| Lauric acid amide propylbetaine | 0.05 |
| Laurylhydroxysulfobetaine | 0.05 |
| Lauric acid | 0.04 |
| Phosphoric acid (75%) | Amount required to adjust second agent to pH 3.8 |
| Dense Glycerol | 30.0 |
| Hydrogen peroxide (35%) | 16.3 |
| Purified Water | balance |

The following evaluation criteria can be applied:
Evaluation Criteria for Foaming
"Superior": Extremely uniform fine foam
"Good": Uniform fine foam
"Normal": Non-uniform coarse foam
"Poor": Foam not formed; moisture admixed.
Evaluation Criteria for Foam Duration
"Superior": Extremely long duration; foam lasted while being allowed to stand.
"Good": Sufficient duration; foam lasted for some time following application.
"Normal": Foam showed sufficient duration so that there was no problem in application; however, foam quickly disappeared following application.
"Poor": Foam disappeared immediately following discharge, and liquid dripping occurred during application.
Evaluation Criteria for Irritation of Scalp
"Superior": No feeling of irritation
"Good": Almost no feeling of irritation
"Normal": Irritation felt, but not at a level that could not be endured.
"Poor": Severe irritation felt.
Evaluation Criteria for Irregular Hair Bleaching
"Superior": Extremely uniform hair bleaching possible without any irregular hair bleaching.
"Good": Uniform hair bleaching possible with hardly any irregular hair bleaching.
"Normal": Slight irregularity in hair bleaching
"Poor": Major irregularity in hair bleaching
Evaluation Criteria for Coating Properties (Ease of Application, Affinity for Hair)
"Superior": Agents firmly penetrated to roots merely by pressing the foam on the hair.
"Good": Agents could easily be caused to penetrate to roots by kneading with hands.
"Normal": Cases occurred in which penetration of the agents was difficult depending on location, as in the roots on the back portion of the head where the quantity of hair was large.
"Poor": Poor penetration; failure to coat roots and the like.

TABLE 7

|  | A: Squeeze foamer | B: Pump foamer | C: Electric foam generator |
|---|---|---|---|
| Foaming | Good | Superior | Superior |
| Foam duration | Good | Superior | Superior |

TABLE 7-continued

|  | A: Squeeze foamer | B: Pump foamer | C: Electric foam generator |
|---|---|---|---|
| Irritation of scalp | Good | Good | Good |
| Irregular hair bleaching | Superior | Superior | Superior |
| Coating properties | Good | Superior | Superior |
| Scattering of agents | none | none | none |

It is seen in Table 7 that there is no scattering of the agents, hair bleaching is possible without irregularity, and scalp irritation is not a problem, when any of the foamer vessels A, B and C are used.

Furthermore, in the case of hair with conspicuous differences in color (brightness) between black hair in areas of new growth and bleached hair from which color is removed (as time elapses following the final hair bleaching), this difference is eliminated, so that a natural finish is obtained, regardless of the foamer vessel that is used.

Example 6

Hair Cosmetic Product for Hair Dyeing

A first agent and second agent are prepared using the compositions shown in Table 8; the first and second agents are placed in a squeeze foamer A and mixed at a mixture ratio (weight ratio) of 1.0:1.5, and these agents are then discharged in the form of foam. 80 g of the discharged foam is applied to the hair as a whole; hair dyeing is accomplished by allowing this foam to stand for 30 minutes, and then rinsing the foam away. There is no scattering of the agents, hair dyeing is accomplished without irregularity, and scalp irritation is not a problem.

Furthermore, differences in color between black hair in areas of new growth and the color of the hair in already dyed areas is eliminated, so that a natural finish can be obtained.

TABLE 8

| First agent | Concentration in first agent (wt%) |
|---|---|
| Strong aqueous ammonia (28%) | 8.0 |
| Ammonium hydrogencarbonate | 14.0 |
| Methyl para-oxybenzoate | 0.1 |
| Fragrance | 0.5 |
| Ascorbic acid | 0.3 |
| Anhydrous sodium sulfite | 0.4 |
| Oxidation dye: Toluene-2,5-diamine solvent (20%) | 0.5 |
| Resorcine | 0.4 |
| Purified Water | balance |
| Second agent | Concentration in second agent (wt %) |
| Sodium polyoxyethylene lauryl ether sulfate | 1.4 |
| Lauric acid amide propylbetaine | 0.05 |
| Laurylhydroxysulfobetaine | 0.05 |
| Lauric acid | 0.04 |
| Phosphoric acid (75%) | Amount required to adjust second agent to pH 3.8 |
| Dense Glycerol | 30.0 |
| Hydrogen peroxide (35%) | 16.3 |
| Purified Water | balance |

Examples 7

Hair Cosmetic Products for Hair Dyeing

A first agent and second agent are prepared using the compositions shown in Table 9; the first and second agents are placed in a squeeze foamer A and mixed at a mixture ratio (weight ratio) of 1.0:1.5, and these agents are then discharged in the form of foam. The overall hair is dyed in the same manner as in Example 6 using 80 g of the discharged foam. There is no scattering of the agents, hair dyeing is accomplished without irregularity, and scalp irritation is not a problem.

Furthermore, differences in color between black hair in areas of new growth and the color of the hair in already dyed areas are eliminated, so that a natural finish can be obtained.

TABLE 9

| First agent | Concentration in first agent (wt %) |
| --- | --- |
| Strong aqueous ammonia (28%) | 8.0 |
| Ammonium hydrogencarbonate | 14.0 |
| Methyl para-oxybenzoate | 0.1 |
| Fragrance | 0.5 |
| Ascorbic acid | 0.3 |
| Anhydrous sodium sulfite | 0.4 |
| Oxidation dye: Toluene-2,5-diamine solvent (20%) | 0.5 |
| Resorcine | 0.4 |
| Sodium polyoxyethylene lauryl ether sulfate | 1.4 |
| Lauric acid amide propylbetaine | 0.05 |
| Laurylhydroxysulfobetaine | 0.05 |
| Lauric acid | 0.04 |
| Purified Water | balance |
| Second agent | Concentration in second agent (wt %) |
| Phosphoric acid (75%) | Amount required to adjust second agent to pH 3.8 |
| Dense Glycerol | 30.0 |
| Hydrogen peroxide (35%) | 16.3 |
| Purified Water | balance |

According to the present invention, a hair cosmetic product in which a two agent type hair bleach or a two agent type hair dye is discharged in the form of foam from a non-aerosol type foamer vessel is provided.

The foam of this two agent type hair bleach or two agent type hair dye that is discharged from this hair cosmetic product has a foam quality that for example shows good affinity with the hair, and has a sufficient hair bleaching power or hair dyeing power without causing irritation of the scalp or scattering of the agents. Accordingly, the preferred hair cosmetic product of the present invention makes it possible to realize a uniform hair bleaching finish or hair dyeing finish with little irregularity.

The present invention provides a hair cosmetic product in which a two agent type hair bleach or two agent type hair dye is discharged in the form of foam from a non-aerosol type foamer vessel. The foam of this two agent type hair bleach or two agent type hair dye that is discharged from this hair cosmetic product has a foam quality that for example shows good affinity with the hair, and has a sufficient hair bleaching power or hair dyeing power without causing irritation of the scalp or scattering of the agents. Accordingly, the preferred hair cosmetic product of the present invention makes it possible to realize a uniform hair bleaching finish or hair dyeing finish with little irregularity.

The entire disclosure of the specification, claims and summary of the Japanese Patent Application No. 2003-122808, filed on Apr. 25, 2003, is hereby incorporated by reference in its entirety.

What is claimed is:

1. A hair treatment method, comprising sequentially
   i) preparing a hair cosmetic by mixing a first agent comprising an alkali agent and a second agent comprising hydrogen peroxide to form a mixed liquid;
   ii) discharging said mixed liquid in the form of a foam from a foamer vessel without a propellant;
   iii) applying said mixed liquid to hair;
   iv) allowing said mixed liquid to stand for 3 to 60 minutes; and
   v) rinsing said mixed liquid away;
   wherein at least one of said first agent and said second agent comprises a surfactant,
   wherein said hair cosmetic is selected from the group consisting of a two agent hair bleach or a two agent dye, and
   wherein said mixed liquid has a viscosity of 1 to 300 mPa·s at 25° C. and a pH of 8 to 11.

2. The hair treatment method according to claim 1, wherein said mixed liquid comprises said surfactant in an amount of 0.1 to 10% by weight of said mixed liquid.

3. The hair treatment method according to claim 1, wherein each of said first agent and said second agent is filled in a container other than said foamer vessel, and upon use, said first agent and said second agent are introduced into said foamer vessel and mixed.

4. The hair treatment method according to claim 1, wherein one of said first agent and said second agent is filled in said foamer vessel, and the other is filled in a container other than said foamer vessel, and upon use, the other is introduced into said foamer vessel and mixed.

5. The hair treatment method according to claim 3 or 4, wherein said first agent is filled in a container resistant to oxygen permeation and said second agent is filled in a container with gas permeability.

6. The hair treatment method according to claim 1, wherein said foam is applied to hair by use of a hand or a tool.

7. The hair treatment method according to claim 6, wherein said foam is applied to the hair by use of a hand.

8. The hair treatment method according to claim 1, wherein said foam is applied to hair not subjected to a blocking treatment.

9. The hair treatment method according to claim 1, wherein said mixed liquid has a pH of 9 to 11.

10. The hair treatment method according to claim 1, wherein said first agent comprises an oxidation dye or a direct dye.

11. The hair treatment method according to claim 1, wherein said mixed liquid further comprises a nonvolatile hydrophilic solvent in an amount of 0.1 to 30% by weight of the mixed liquid.

12. The hair treatment method of claim 1, wherein said hair cosmetic product is a two agent hair bleach.

13. The hair treatment method of claim 1, wherein said hair cosmetic product is a two agent hair dye.

14. The hair treatment method of claim 1, wherein said mixed liquid has a viscosity of 10 to 200 mPa·s at 25° C.

* * * * *